(12) United States Patent
Blanco et al.

(10) Patent No.: US 9,121,048 B1
(45) Date of Patent: Sep. 1, 2015

(54) PROTECTION AGAINST HUMAN RHINOVIRUS INFECTION

(71) Applicant: Sigmovir Biosystems, Inc., Rockville, MD (US)

(72) Inventors: Jorge C. G. Blanco, Washington, DC (US); Adriana E. Kajon, Albuquerque, NM (US)

(73) Assignees: Sigmovir Biosystems, Inc., Rockville, MD (US); Lovelace Respiratory Research Institute, Albuquerque, NM (US)

(*) Notice: Subject to any disclaimer, the term of this patent is extended or adjusted under 35 U.S.C. 154(b) by 60 days.

(21) Appl. No.: 14/026,485

(22) Filed: Sep. 13, 2013

Related U.S. Application Data

(60) Provisional application No. 61/775,511, filed on Mar. 9, 2013, provisional application No. 61/701,546, filed on Sep. 14, 2012.

(51) Int. Cl.
*C12Q 1/02* (2006.01)

(52) U.S. Cl.
CPC ..................................... *C12Q 1/025* (2013.01)

(58) Field of Classification Search
None
See application file for complete search history.

(56) References Cited

PUBLICATIONS

Palmenberg et al. (Science. 2009; 324 (3): 55-59).*
Privolizzi et al. (Antiviral Chemistry and Chemotherapy. 2014; 23: 173-177).*
Boukhvalova et al. (Biologicals. 2009; 37: 152-159).*
Register et al. (Journal of Virology. 1991; 65 (12): 6589-6596).*
Rouan et al. (Antimicrobial Agents and Chemotherapy. 2010; 54 (11): 4534-4539).*
Arruda, E. et al., Frequency and Natural History of Rhinovirus Infections in Adults during Autumn, Journal of Clinical Microbiology, Nov. 1997, 35(11):2864-2868.
Bartlett, N.W. et al., Mouse Models of Rhinovirus-Induced Disease and Exacerbation of Allergic Airway Inflammation, Nature Medicine, Feb. 2008, 14(2):199-204.
Blanco, J.C.G. et al., The Cotton Rat: An Underutilized Animal Model for Human Infectious Diseases Can Now Be Exploited Using Specific Reagents to Cytokines, Chemokines, and Interferons, Journal of Interferon & Cytokine Research, 2004, 24:21-28.
Blanco, J.C.G. et al., Receptor Characterization and Susceptibility of Cotton Rats to Avian and 2009 Pandemic Influenza Virus Strains, Journal of Virology, Feb. 2013, 87(4):2036-2045.
Bossios, A. et al., Rhinovirus Infection and House Dust Mite Exposure Synergize in Inducing Bronchial Epithelial Cell Interleukin-8 Release, Clinical and Experimental Allergy, 2008, 38:1615-1626.
Bush, R.K. et al., Effects of Experimental Rhinovirus 16 Infection on Airways and Leukocyte Function in Normal Subjects, Journal of Allergy and Clinical Immunology, Feb. 1978, 61(2):80-87.
Gielen, V. et al., Azithromycin Induces Anti-Viral Responses in Bronchial Epithelial Cells, European Respiratory Journal, 2010, 36:646-654.
Holgate, S.T., Pathophysiology of Asthma: What Has Our Current Understanding Taught Us About New Therapeutic Approaches?, Journal of Allergy and Clinical Immunology, Sep. 2011, 128(3):495-505.
The Impact-RSV Study Group, Palivizumab, a Humanized Respiratory Syncytial Virus Monoclonal Antibody, Reduces Hospitalization From Respiratory Syncytial Virus Infection in High-Risk Infants, Pediatrics, Sep. 1998, 102(3):531-537.
Iwane, M.K. et al., Human Rhinovirus Species Associated With Hospitalizations for Acute Respiratory Illness in Young US Children, The Journal of Infectious Diseases, 2011, 204:1702-1710.
Jacobs, S.E. et al., Human Rhinoviruses, Clinical Microbiology Reviews, Jan. 2013, 26(1):135-162.
Kaiser, L. et al., Chronic Rhinoviral Infection in Lung Transplant Recipients, American Journal of Respiratory Critical Care Medicine, 2006, 174:1392-1399.
Korpi-Steiner, N.L. et al., Human Rhinovirus Induces Robust IP-10 Release by Monocytic Cells, Which is Independent of Viral Replication but Linked to Type I Interferon Receptor Ligation and STAT1 Activation, Journal of Leukocyte Biology, Dec. 2006, 80:1364-1374.
Korpi-Steiner, N.L. et al., Human Monocytic Cells Direct the Robust Release of CXCL10 by Bronchial Epithelial Cells During Rhinovirus Infection, Clinical & Experimental Allergy, 2010, 40:1203-1213.
Lee, W.-M. et al., Complete Sequence of the RNA Genome of Human Rhinovirus 16, a Clinically Useful Common Cold Virus Belonging to the ICAM-1 Receptor Group, Virus Genes, 1994, 9(2)177-181.
Louie, J.K. et al., Rhinovirus Outbreak in a Long Term Care Facility for Elderly Persons Associated with Unusually High Mortality, Clinical Infectious Diseases, Jul. 2005, 41:262-265.
Mallia, P. et al., An Experimental Model of Rhinovirus Induced Chronic Obstructive Pulmonary Disease Exacerbations: A Pilot Study, Respiratory Research, 2006, 7:116-125.
McLean, G.R. et al., Rhinovirus Infections and Immunisation Induce Cross-Serotype Reactive Antibodies to VP1, Antiviral Research, 2012, 95:193-201.
Makela, M.J. et al., Lack of Induction by Rhinoviruses of Systemic Type I Interferon Production or Enhanced MxA Protein Expression During the Common Cold, European Journal of Clinical Microbiology and Infectious Disease, 1999, 18:665-668.
Ottolini, M.G. et al., The Cotton Rat Provides a Useful Small-Animal Model for the Study of Influenza Virus Pathogenesis, Journal of General Virology, 2005, 86:2823-2830.
Pfeuffer, J. et al., Extent of Measles Virus Spread and Immune Suppression Differentiates between Wild-Type and Vaccine Strains in the Cotton Rat Model (Sigmodon hispidus), Journal of Virology, Jan. 2003, 77(1):150-158.
Pinto, C.A. et al., Experimental Infection of Gibbons with Rhinovirus, Nature, Dec. 1969, 224:1310-1311.
Pletneva, L.M. et al., Induction of Type I Interferons and Interferon-Inducible Mx Genes During Respiratory Syncytial Virus Infection and Reinfection in Cotton Rats, Journal of General Virology, 2008, 89:261-270.
The Prevent Study Group, Reduction of Respiratory Syncytial Virus Hospitalization Among Premature Infants and Infants With Bronchopulmonary Dysplasia Using Respiratory Syncytial Virus Immune Globulin Prophylaxis, Pediatrics, Jan. 1997, 99(1):93-99.

(Continued)

*Primary Examiner* — Shanon A Foley
(74) *Attorney, Agent, or Firm* — George W. Cox

(57) ABSTRACT

Methods, kits, and compositions are disclosed for vaccinating a human or animal against human rhinovirus infection. Also provided are methods of using a cotton rat model for identifying and testing vaccines and therapeutic agents that prevent or ameliorate human rhinovirus infection.

10 Claims, 14 Drawing Sheets

(56) References Cited

PUBLICATIONS

Prince, G.A. et al., Mechanisms of Immunity to Respiratory Syncytial Virus in Cotton Rats, 1983, 42(1):81-87.
Proud, D. et al., Gene Expression Profiles During in Vivo Human Rhinovirus Infection, American Journal of Respiratory Critical Care Medicine, 2008, 178:962-968.
Savolainen, C. et al., Genetic Clustering of All 102 Human Rhinovirus Prototype Strains: Serotype 87 is Close to Human Enterovirus 70, Journal of General Virology, 2002, 83:333-340.
Seemungal, T.A.R. et al., Detection of Rhinovirus in Induced Sputum at Exacerbation of Chronic Obstructive Pulmonary Disease, European Respiratory Journal, 2000, 16:677-683.
Simmonds, P. et al., Proposals for the Classification of Human Rhinovirus Species C into Genotypically Assigned Types, Journal of General Virology, 2010, 91:2409-2419.
Sykes, A. et al., Rhinovirus 16-Induced IFN-a and IFN-b are Deficient in Bronchoalveolar Lavage Cells in Asthmatic Patients, Journal of Allergy and Clinical Immunology, Jun. 2012, 129(6):1506-1514.e6.
Winther, B., Rhinovirus Infections in the Upper Airway, Proceedings of the American Thoracic Society, 2011, 8:79-89.
Blomqvist, S. et al., Virological and Serological Analysis of Rhinovirus Infections During the First Two Years of Life in a Cohort of Children, Journal of Medical Virology, 2002, 66:263-268.
Dick, E.C., Experimental Infection of Chimpanzees with Human Rhinovirus Types 14 and 43 (32875), Proceedings of the Society of Experimental Biology and Medicine, 1968, 127:1079-1081.
Falah, N. et al., Ex Vivo and in Vivo Inhibition of Human Rhinovirus Replication by a New Pseudosubstrate of Viral 2A Protease, Journal of Virology, 2012, 86(2):691-704.
Haller, O. et al., Interferon-Induced Mx Proteins: Dynamin-Like GTPases with Antiviral Activity, Traffic, 2002, 3:710-71.
Hamelin, M.-E. et al., Pathogenesis of Human Metapneumovirus Lung Infection in BALB/c Mice and Cotton Rats, Journal of Virology, Jul. 2005, 79(14):8894-8903.
Hamparian, V.V. et al., Recovery of New Viruses (Coryzavirus) from Cases of Common Cold in Human Adults (26962), Proceedings of the Society of Experimental Biology and Medicine, 1961, 108:444-453.
Hamparian, V.V. et al., A Collaborative Report: Rhinoviruses—Extension of the Numbering System from 89-100, Virology, 1987, 159:191-192.
Ledford, R.M. et al., VP1 Sequencing of All Human Rhinovirus Serotypes: Insights into Genus Phylogeny and Susceptibility to Antiviral Capsid-Binding Compounds, Journal of Virology, 2004, 78(7):3663-3674.
Yin, F.H. et al. Establishment of a Mouse Model for Human Rhinovirus Infection, Journal of General Virology, 1986, 67:2335-2340.
Ottolini, M. et al., Combination Anti-Inflammatory and Antiviral Therapy of Influenza in a Cotton Rat Model, Pediatric Pulmonology, 2003, 36:290-294.
Pacini, D.L. et al., A New Animal Model for Human Respiratory Tract Disease Due to Adenovirus, The Journal of Infectious Diseases, Jul. 1984,150(1):92-97.
Porter, D.D. et al., Pathogenesis of Human Parainfluenza Virus 3 Infection in Two Species of Cotton Rats: Sigmodon hispidus Develops Bronchiolitis, While Sigmodon fulviventer Develops Interstitial Pneumonia, Journal of Virology, Jan. 1991, 65(1):103-111.
Prince, G.A. et al., Vaccine-enhanced respiratory syncytial virus disease in cotton rats following immunization with Lot 100 or a newly prepared reference vaccine, Journal of General Virology, 2001, 82:2881-2888.
Stertz, S. et al., The Antiviral Potential of Interferon-Induced Cotton Rat Mx Proteins Against Orthomyxovirus (Influenza), Rhabdovirus, and Bunyavirus, Journal of Interferon & Cytokine Research, 2007, 27:847-855.
Tsai, J.C. et al., An Experimental Animal Model of Adenovirus-Induced Ocular Disease, Archives of Ophthalmology, Aug. 1992, 110:1167-1170.
Williams, J.V. et al., The Cotton Rat (Sigmodon hispidus) Is a Permissive Small Animal Model of Human Metapneumovirus Infection, Pathogenesis, and Protective Immunity, Journal of Virology, 2005, 79(17):10944-10951.
Winther, B. et al., Light and Scanning Electrol Microscopy of Nasal Biopsy Material from Patients with Naturally Acquired Common Colds, Acta Otolaryngology, 1984, 97:309-318.
Winther, B. et al., Respiratory Virus Infection of Monolayer Cultures of Human Nasal Epithelial Cells, American Review of Respiratory Diseases, 1990, 141:839-845.
Wyde, P.R. et al., Measles Virus Replication in Lungs of Hispid Cotton Rats after Intranasal Inoculation (43483), Proceedings of the Society of Experimental Biology and Medicine, 1992, 201:80-87.

* cited by examiner

PROTECTION AGAINST HUMAN RHINOVIRUS INFECTION

CROSS-REFERENCE TO RELATED APPLICATIONS

This application claims the benefit of U.S. Provisional Patent Application Ser. No. 61/701,546, filed Sep. 14, 2012, and U.S. Provisional Patent Application Ser. No. 61/775,511, filed Mar. 9, 2013, each of which is hereby incorporated by reference in its entirety.

STATEMENT AS TO RIGHTS TO INVENTIONS MADE UNDER FEDERALLY SPONSORED RESEARCH OR DEVELOPMENT

This invention was made with U.S. Government support under Grant No. R21 AI101480, awarded by the National Institutes of Health. The Government has certain rights in this invention.

NAMES OF PARTIES TO A JOINT RESEARCH AGREEMENT

Sigmovir Biosystems, Inc. and Lovelace Respiratory Research Institute.

This application incorporates by reference the Sequence Listing contained in an ASCII text file named "14 026485 ST25.txt" submitted via EFS-Web. The text file was created on Apr. 10, 2015, and is 1.10 kb in size.

BACKGROUND OF THE INVENTION

The present invention relates generally to protection against rhinovirus infection. While the invention is subject to a wide range of applications, it is especially suited for vaccination of animals and humans against human rhinovirus infection and the prevention of associated illnesses. In addition, the invention provides methods of identifying and testing vaccines and therapeutics for the prevention and amelioration of human rhinovirus infection and associated illnesses and, thereby, provides methods of determining the efficacy of vaccines and therapeutics against human rhinovirus.

Human rhinoviruses (HRV) represent the single most important etiological agents of the common cold and the most frequent cause of acute respiratory infection in humans (Arruda et al., *J. Clin. Microbiol.* 35:2864, 1997; Turner and Couch, *Rhinoviruses*, Vol. 1, Lippincott-Williams & Wilkins, Philadelphia, Pa., 2007). HRV are single-stranded RNA viruses members of the Picornaviridae family, genus enterovirus, which also include polioviruses and coxsackieviruses. The increasing use of molecular methods for respiratory virus detection and characterization has contributed to cluster the HRV prototype strains into three genetic species: HRV-A, HRV-B (Savolainen et al., *J. Gen. Virol.* 83:333, 2002), and the recently identified HRV-C (Simmonds et al., *J. Gen. Virol.* 91:2409, 2013). HRV-A and HRV-B comprise a number of antigenically distinct viruses designated on the basis of their cross-neutralization properties in vitro, and currently totaling 75 serotypes of HRV-A and 25 serotypes of HRV-B (Hamparian et al., *Virology* 159:191, 1987; Kapikian et al., *Nature* 213:761, 1967; Ledford et al., *J. Virol.* 78:3663, 2004). Viruses corresponding to the HRV-C species do not grow in standard cell culture (for example, HeLa or embryonic fibroblasts) but are now known to be highly prevalent and widely circulating worldwide.

HRV16 belongs to the species HRV-A also known as the major group. HRV16 uses the well-characterized intercellular adhesion molecule-1 (ICAM-1) receptor for attachment and entry (Lee et al., *Virus Genes* 9:177, 1995), and has been a model virus for studying transmission of rhinoviruses (D'Alessio et al., *J. Infect. Dis.* 133:28, 1976), pathogenesis of the common cold (Bush et al., *J. Allergy Clin. Immunol.* 61:80, 1978), virus-induced asthma and chronic obstructive pulmonary disease (COPD) (Malia et al., *Respir. Res.* 7:116, 2006; Bossios et al., *Clin. Exp. Allergy* 38:1615, 2008; Sykes et al., *J. Allergy Clin. Immunol.* 129:1506, 2012), and evaluation of anti-rhinovirus drugs in human volunteers because it reproducibly induces strong symptoms in human subjects. Currently, HRV16 is also widely used for in vitro studies aiming to define the molecular mechanisms by which rhinovirus infection of respiratory epithelial cell triggers the overwhelming inflammation in airways (Korpi-Steiner et al., *J. Leukoc. Biol.* 80:1364, 2006; Korpi-Steiner et al, *Clin. Exp. Allergy* 40:1203, 2008).

Until now, three different cell-surface receptors have been shown to be used by rhinoviruses. Rhinovirus type 87 appears to use the decay-accelerating receptor factor as a receptor (Blomqvist et al., *J. Clin. Microbiol.* 40:4218, 2002). The minor group receptor, low-density lipoprotein (LDL), is used by at least ten serotypes (1A, 1B, 2, 29, 30, 31, 44, 47, 49, and 62), and the ICAM-1 receptor is used by the remaining described serotypes of the major group including HRV16.

HRV infection is typically responsible for upper respiratory symptoms including rhinorrhea, sore throat, nasal congestion, sneezing, cough, and headache. More importantly, HRV has emerged as the most frequent pathogen associated with exacerbation episodes in asthmatic (Holgate, *J. Allergy Clin. Immunol.* 118:587, 2006) and COPD patients (Seemungal et al., *Eur. Respir. J.* 16:677, 2000). Several avenues have been followed towards the development of preventive and therapeutic strategies against HRV infections. However, due to the occurrence of more than 100 HRV serotypes with high sequence variability in the antigenic sites, no rhinovirus vaccine and no HRV-specific antiviral drug are currently available. Furthermore, although it is clear that animal models to test the efficacy of HRV vaccination or therapy in vivo would be important assets, most efforts to develop such resources have resulted in mouse models of limited value.

A major characteristic of HRV is their high host species specificity attributable, for the major group viruses, primarily to the use of ICAM-1 as a receptor. Chimpanzees have been successfully infected with HRV14 and 43, and gibbons with HRV1A, 2 and 14, but no overt illness was observed in the infected animals (Pinto and Haff, *Nature* 224:1310, 1969; Dick, *Proc. Soc. Exp. Biol. Med.* 127:1079, 1968). Infection was not demonstrated in rabbits, guinea pigs, weanling mice, or 1-day-old mice infected with HRV by the subcutaneous, intraperitoneal, or intravenous routes. Similarly, intracranial injections into monkeys, hamsters, or baby mice did not result in either infection or disease (Hamparian et al., *Proc. Soc. Exp. Biol. Med.* 108:444, 1961; Kisch et al., *Am. J. Hyg.* 79:125, 1964). Intranasal inoculation of ferrets, hamsters, and baby mice was also investigated without effects. HRV2 was adapted to grow in L cells and used in mice, but limited replication was demonstrated (Yin and Lomax, *J. Gen. Virol.* 67:2335, 1986). The BALB/c mouse was proposed recently as a model for rhinovirus-induced disease and exacerbation of allergic airway inflammation (Bartlett et al., *Nat. Med.* 14:199, 2008). Using HRV1B, it was demonstrated that infection is localized in the lungs, induces airway and pulmonary inflammation, and mucin production despite low viral replication. In addition, a model for HRV16 pathogenesis was presented using transgenic mice expressing a human/mouse ICAM-1 chimeric receptor (Bartlett et al., *Nat. Med.* 14:199, 2008). This model showed low levels of viral replication similar to HRV in BALB/c mice. Virus replication in the upper respiratory tract (URT) was not analyzed in either model. Balb/c mice were also recently used for testing antiviral drugs against HRV2 (Falah et al., *J. Virol.* 86:691, 2012). To date, no human rhinovirus vaccination/challenge/protection studies have been performed and validated in any animal model. Thus, the feasibility of preclinical studies in animal models for testing the efficacy of anti-rhinovirus vaccines and therapeutics has been severely hampered.

The morbidity and mortality attributable to rhinovirus infection is considerable and results in billions of dollars of health care cost every year. Despite the significance of the problem, no effective prevention of HRV infection or treatment of HRV-associated disease is currently available. Attempts to develop a small animal model of HRV infection in many species have failed, thus severely hampering mechanistic studies and the development of vaccines and therapeutics against HRV infection. Over the years, the cotton rat (*Sigmodon hispidus*) has been shown to support replication of a broad spectrum of human viruses including respiratory syncytial virus (RSV) (Prince et al., *Am. J. Pathol.* 93:771, 1978), non-adapted strains of human and avian influenza (Blanco et al., *J. Virol.* 87:2036, 2013; Ottolini et al., *Pediatr. Pulmonol.* 36:290, 2003; Ottolini et al., *J. Gen. Virol.* 86:2823, 2005), measles (Pfeuffer et al., *J. Virol.* 77:150, 2003; Wyde et al., *Proc. Soc. Exp. Biol. Med.* 201:80, 1992), several adenovirus serotypes (Pacini et al., *J. Infect. Dis.* 150:92, 1984; Prince et al., *J. Virol.* 67:101, 1993; Tsai et al., *Arch. Ophthalmol.* 110:1167, 1992), parainfluenza virus type 3 (Porter et al., *J. Virol.* 65:103, 1991), and human metapneumovirus (Wyde et al., *Antiviral Res.* 66:57, 2005) (Hamelin et al., *J. Gen. Virol.* 88:3391, 2007; Williams et al., *J. Virol.* 79:10944, 2005). The cotton rat is well-recognized for its pivotal role in the development of the only effective prophylactic treatments against RSV disease (RespiGam® and Synagis®). However, to date, there is no report that the cotton rat can support the replication of HRV.

There is no vaccine against human rhinovirus, and there is no specific therapy against human rhinovirus infection and associated illnesses. Thus, there remains a need for safe and effective approaches to protect animals and humans against human rhinoviruses. In particular, there remains a need for specific vaccines to prevent human rhinovirus infection, and for therapeutics to ameliorate myriad illnesses associated with rhinovirus infection. In addition, there remains an unfulfilled need for experimental methods and approaches for identifying (and determining the efficacy of) vaccines and therapeutic agents against human rhinovirus.

SUMMARY OF THE INVENTION

Accordingly, an object of the invention is to provide a method of vaccinating an animal or human against human rhinovirus. In one representative embodiment, a method is provided for administering an effective amount of at least one type of human rhinovirus to a susceptible subject at least one time. In other representative embodiments, more than one administration is performed over the course of several days, weeks, months, or years to provide initial and continual immunity against human rhinovirus. In one embodiment, the human rhinovirus is human rhinovirus 16 (HRV16). In alternative embodiments, the human rhinovirus may be, for example, human rhinovirus A, human rhinovirus B, human rhinovirus C, or any serotype of the various genetic species of human rhinoviruses. In one aspect, administration of the rhinovirus is achieved intramuscularly (i.m.). Alternatively, administration of the rhinovirus may be achieved, for example, intravenously (i.v.), intradermally (i.d.), subcutaneously (s.q.), or orally. In further embodiments, at least one type of human rhinovirus is administered simultaneously with at least one other antigen. In an alternative embodiment, at least one type of human rhinovirus is administered before at least one other antigen. In another alternative embodiment, at least one type of human rhinovirus is administered after at least one other antigen. In still other aspects, at least one type of human rhinovirus is administered with at least one adjuvant. In other aspects, at least one other antigen is administered with at least one adjuvant. The human rhinovirus(es) of the invention may be, for example, a component of a vaccine formulation or composition.

Another object of the invention is to provide a method of inducing the production of antibodies (for example, serum antibodies) against rhinovirus in an animal or human. In a representative embodiment, an animal or human is immunized with live rhinovirus. In an aspect of the invention, the serum antibodies generated following immunization of the animal or human are suitable, for example, for passive immunization of an animal or human. As such, the serum antibodies are suitable for passive immunization of an animal or human when the serum antibodies are administered, for example, parenterally. Alternatively, the serum antibodies are suitable for passive immunization of an animal or human when the serum antibodies are administered orally. In still another aspect, the serum antibodies are suitable for passive immunization of an animal or human when the serum antibodies are administered in the presence of milk. In one embodiment, the serum antibodies are suitable for passage from immunized mothers to their offspring through lactation. In another embodiment, the serum antibodies are suitable for passage from immunized mothers to their offspring through the placenta. In each instance of passage of antibodies via lactation or placenta, when the serum antibodies are passed from an immunized mother to her offspring, the serum antibodies protect the offspring against human rhinovirus infection and rhinovirus-associated illnesses. In one representative embodiment, a rhinovirus-associated illness is asthma. In other aspects, a rhinovirus-associated illness may be, for example, any respiratory illness known to manifest following rhinovirus infection of an animal or human.

A further object of the invention is to provide a method of identifying and testing a vaccine or therapeutic agent that prevents or ameliorates rhinovirus infection. In a representative embodiment, a cotton rat is challenged with rhinovirus intranasally (for example, twenty one days) after administration of a potential rhinovirus vaccine or therapeutic agent. The titer of rhinovirus present in tissue (for example, lung, nose, or trachea) derived from the challenged cotton rat is measured and compared with the titer of rhinovirus in tissue (for example, lung, nose, or trachea) derived from a cotton rat challenged with rhinovirus intranasally (i.n.) (for example, twenty one days) after administration of a control agent. The control agent can be, for example, saline, phosphate buffered saline (PBS), an inert aqueous isotonic solution, and the like. A decrease in the titer of rhinovirus in tissue from an animal administered the potential vaccine or therapeutic agent as compared to the titer of rhinovirus measured in tissue from an animal administered the control agent (for example, PBS) indicates the identification of a vaccine or therapeutic agent that prevents rhinovirus infection. In one aspect, the potential rhinovirus vaccine or therapeutic agent may be, for example, a native protein or a fragment thereof. In another aspect, the potential rhinovirus vaccine or therapeutic agent may be, for example, a recombinant protein or a fragment thereof. Further still, the potential rhinovirus vaccine or therapeutic agent may be a nucleic acid. Alternatively, the potential rhinovirus vaccine or therapeutic agent may be, for example, a biological molecule such as a receptor molecule. In yet another aspect, the potential rhinovirus vaccine or therapeutic agent may be a small molecule such as a synthesized chemical entity. In a representative embodiment, the potential rhinovirus vaccine or therapeutic agent may be administered, for example, i.m., i.d., i.v., s.q., or orally.

Another object of the invention is to provide a kit for immunizing a subject against rhinovirus. In a representative embodiment, the kit includes a live human rhinovirus. In another representative embodiment, the kit includes a live human rhinovirus composition. In one aspect, the live rhinovirus or live rhinovirus composition may be (or may include), for example, wild type human rhinovirus. In another aspect, the live rhinovirus or live rhinovirus composition may be (or may include), for example, recombinant human rhinovirus. Further still, the live rhinovirus or live rhinovirus composition may be (or may include), for example, a combination of wild type human rhinovirus and recombinant human rhinovirus. One skilled in the art would understand that kits and packages may be prepared comprising one, all, or any combination of live rhinovirus, rhinovirus composition, diluent, buffer, adjuvant, pharmaceutically-acceptable carrier, other antigen, biological agent, chemical entity, nucleic acid, protein, and fragments thereof.

Another object of the invention is to provide a vaccine composition comprising human rhinovirus that elicits a prophylactically effective (and/or a therapeutically effective) immune response in an animal or human against human rhinovirus. In one representative embodiment, the human rhinovirus is live human rhinovirus. In alternative embodiments, the human rhinovirus may be, for example, killed or attenuated human rhinovirus. In one aspect, the human rhinovirus is HRV16. In certain embodiments, the vaccine composition may include, for example, wild type human rhinovirus, clinical isolate of human rhinovirus, recombinant human rhinovirus, rhinovirus-associated proteins or fragments thereof, other antigens, receptor molecules, adjuvants, carriers, diluents, nucleic acids, and small molecules, which may be added individually or in combination.

These and other objects are achieved in the invention.

The present invention fulfills a long felt need in the fields of respiratory virus research and infectious disease medicine. The invention overcomes major disadvantages and deficiencies of prior art approaches and current vaccination protocols directed to the prevention of myriad respiratory illnesses, by providing methods, kits, and compositions for vaccinating animals and humans against human rhinovirus as well as for identifying and testing vaccines and therapeutic agents that prevent rhinovirus infection and rhinovirus-associated illnesses.

There has thus been outlined, rather broadly, features of the invention in order that the detailed description thereof that follows may be better understood, and in order that the present contribution to the art may be better appreciated. There are, of course, additional features of the invention that will be described further hereinafter. Indeed, it is to be understood that both the foregoing general description and the following detailed description are exemplary and explanatory and are intended to provide further explanation of the invention as claimed.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other methods, systems, kits, and compositions for carrying out the several purposes of the present invention. It is important, therefore, that equivalent constructions insofar as they do not depart from the spirit and scope of the present invention, are included in the present invention.

The accompanying drawings are included to provide a further understanding of the invention and are incorporated in and constitute a part of this specification, illustrate several embodiments of the invention, and together with the description serve to explain the principles of the invention.

BRIEF DESCRIPTION OF THE DRAWINGS

FIG. 1 shows characteristics of cotton rats infected with $10^7$ plaque forming units (PFU) of HRV16 intranasally.

FIG. 2 shows airway disease associated with HRV16 infection in the cotton rat model.

FIG. 3 shows vaccination of cotton rats with live HRV16.

FIG. 5 shows maternal transfer of protection conferred by vaccination.

DETAILED DESCRIPTION OF THE INVENTION

Figure 1A:
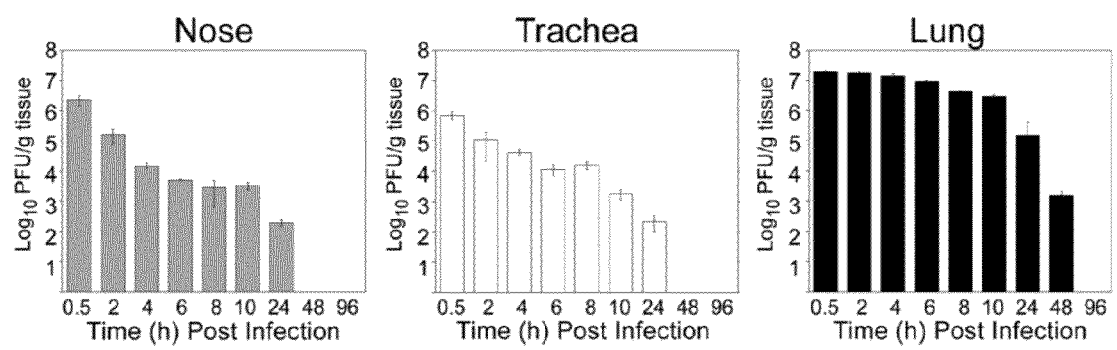
FIG. 1A shows the quantification of viral titers in the nose (left panel), trachea (middle panel), and lung (right panel) homogenates from infected animals at the indicated times in hours (h) post-challenge with HRV16. Groups of 5 to 10 animals were sacrificed at each time in a total of three independent experiments.

Provided herein are methods, kits, and compositions for vaccinating a human or animal against human rhinovirus infection. Also provided are methods for identifying and testing vaccines and therapeutic agents that prevent and/or ameliorate rhinovirus infection. Reference will now be made in detail to representative embodiments of the invention, examples of which are illustrated in the accompanying drawings.

The term "subject" as used herein means, but is not limited to, any animal or human in need of or capable of receiving prophylactic or therapeutic vaccination against human rhinovirus.

The term "vaccine" as used herein means, but is not limited to, a formulation or composition that includes live, killed, inactivated, or attenuated microorganisms, or antigenic proteins (or fragments thereof) obtained from microorganisms. In addition, a vaccine is understood to be a formulation or composition that may include disease-associated proteins (or fragments thereof) obtained from microorganisms. The antigenic components of vaccines may be, for example, recombinant or native proteins (or fragments thereof).

The term "vaccination" as used herein means, but is not limited to, the introduction of a vaccine into a subject for the purpose of inducing a protective immune response against a particular disease or disorder (that is, an immunizing procedure in which vaccine is administered to a subject). For example, "vaccination" includes a process which includes the administration of at least one type of human rhinovirus (such as human rhinovirus A, human rhinovirus B, human rhinovirus C, or any serotype of the various genetic species of human rhinoviruses) alone or in combination with another antigen and/or adjuvant to an animal or human, whereby the administration elicits an immune response in the animal or human against human rhinovirus.

The term "immunization" as used herein means, but is not limited to, the induction of immunity and may include, for example, "active immunization" (which is the stimulation of the immune system to confer protection against a disease or disorder, for example, by administration of a vaccine, toxoid, or microbe) and "passive immunization" (which is where pre-synthesized elements of the immune system (or elements produced in advance), for example, antibodies or cells, are transferred to an animal or human so that the body does not need to produce these elements itself, and occurs physiologically, for example, when antibodies are transferred from mother to fetus during pregnancy or from mother to newborn during lactation and feeding). In some instances herein, the terms vaccination and immunization may be used interchangeably.

The terms "control," "control sample," and "control agent" as used herein have the meaning ascribed them by a person skilled in the art and mean, but are not limited to, a sample or treatment condition that provides an expected positive or negative result compared to an unknown test sample or treatment, potential vaccine, possible new therapeutic agent, experimental condition, or the like.

The term "immune response" as used herein means, but is not limited to, an integrated response to an antigen involving recognition of antigens by specific antibodies and previously sensitized lymphocytes (adaptive immune response) and by cells of the innate immune system (innate immune response).

The term "antigen" as used herein means, but is not limited to, a live, weakened, or killed microorganism (virus or bacterium), parts of the microorganism (native or recombinant), or disease-associated proteins (or fragments thereof, native or recombinant).

The term "antibody" is understood to have its common meaning as understood by a person skilled in the art. An antibody can be a maternal antibody that is transmitted (for example, passed or passaged) from mother to fetus or newborn via the placenta and/or colostrum and breast milk.

The vaccines, antigens, agents, and adjuvants of the invention may optionally be administered via a delayed-release device or method. The term "delayed-release device or method" as used herein means, but is not limited to, any device or method capable of releasing an agent or product (for example, a drug or a vaccine) at a time later than immediately following its administration. Various delayed-release devices have been described (Stubbe et al., *Pharm. Res.* 21:1732, 2004) and could be applicable to the representative embodiments of the invention. Delayed-release devices and methods can be identified and employed without undue experimentation by one skilled in the art after consideration of all criteria and use of best judgment on the subject's behalf.

The vaccines, vaccine compositions, and agents of the embodiments of the invention are administered in a pharmacologically or physiologically acceptable and effective amount to induce an immune response to an antigen. Similarly, the vaccines, vaccine compositions, and agents of the embodiments of the invention are administered in prophylactically or therapeutically effective amounts, which are to be understood as amounts meeting the intended prophylactic or therapeutic objectives, and providing the benefits available from administration of such vaccines, vaccine compositions, and agents.

The term "effective amount" as used herein means, but is not limited to, a concentration capable of inducing humoral immunity, cell-mediated immunity, or a combination of humoral and cell-mediated immunity in a subject, which is sufficient to cure (partly or completely) or prevent disease or disorder caused by an antigen (including, for example, human rhinovirus). For example, an effective amount of vaccine refers to the amount administered to achieve seroconversion and is evidenced such as by the presence of, for example, a two- to four-fold higher level of antigen-specific antibodies in the subject's serum. One skilled in the art would understand the range of immunological responses anticipated by the terms "humoral immunity" and "cell-mediated immunity," such as antibody production and activities, T cell proliferation and activities, and cytokine production and activities. Effective amount is understood to be an amount not harmful to the subject where any harmful side effects are outweighed by the benefits.

In general, the dosage ranges for administration of the vaccines, vaccine compositions, and agents according to the present invention are those that produce the desired effect(s). The useful dosage to be administered will vary depending on the age, weight, and type of subject vaccinated, the mode, route, and schedule of administration, the response of the individual subject, and the type of pathogen/antigen against which vaccination is sought. The dosage will also vary with the nature or the severity of the underlying condition, with epidemiologic conditions, with the concomitant use of other active compounds, and the route of administration. In addition, the dosage will be determined by the existence of any adverse side effects such as local hypersensitivity, systemic adverse effects, and immune tolerance.

An effective dose of the vaccine (and other agent(s)) can be determined without undue experimentation (for example, by pharmacokinetic studies) by one skilled in the art after consideration of all criteria and use of best judgment on the patient's behalf (and will most often be contingent upon the particular vaccine composition utilized). The dosage to be administered will depend upon the particular case, but in any event, it is the amount sufficient to induce a protective antibody and/or cell-mediated immune response against human rhinovirus.

Optionally, one or more compounds having adjuvant activity may be added to the vaccines or vaccine compositions of the invention. The term "adjuvant" as used herein means, but is not limited to, a non-specific stimulator of the immune system. Adjuvants enhance the immune response of the host to the vaccine. Examples of adjuvants known in the art are Freunds Complete and Incomplete adjuvant, Toll-like receptors (TLRs), RIG-like receptors (RLRs), other receptor molecules, receptor ligands and their analogues, vitamin E, nonionic block polymers, muramyl dipeptides, immune stimulating complexes, saponins, mineral oil, vegetable oil, and Carbopol. Adjuvants, especially suitable for mucosal application are, for example, the *E. coli* heat-labile enterotoxin (recombinant or otherwise) and Cholera toxin. Other suitable adjuvants are, for example, aluminum hydroxide, aluminum phosphate or aluminum oxide, oil-emulsions (for example, of Bayol F.sup.(R) or Marcol 52.sup.(R)), and vitamin-E solubilisate. Other adjuvants can include, for example, GPI-0100 (Galenica Pharmaceuticals, Inc., Birmingham, Ala.), water-in-oil emulsion, oil-in-water emulsion, or water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (for example, anhydromamiitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121 (Hunter et al., The Theory and Practical Application of Adjuvants (Ed. Stewart-Tull, D. E. S.). John Wiley and Sons, NY, pp 51-94, 1995; Todd et al., *Vaccine* 15:564, 1997). A further instance of an adjuvant is a compound chosen from the polymers of acrylic or methacrylic acid and the copolymers of maleic anhydride and alkenyl derivative. Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, and IMS 1314, among many others.

The vaccines, vaccine compositions, and agents of the embodiments of the invention may, optionally, be administered in combination with (or may include) one or more pharmaceutically acceptable carriers, diluents, or excipients. Vaccines, vaccination techniques, pharmaceutical compositions, methods of preparing pharmaceutical compositions, and pharmaceutically acceptable carriers, diluents, and excipients are known in the art and are described, for example, in "Remington: The Science and Practice of Pharmacy" (formerly "Remington's Pharmaceutical Sciences," University of the Sciences in Philadelphia, Lippincott, Williams & Wilkins, Philadelphia, Pa. (2005)), the disclosure of which is hereby incorporated by reference. A person skilled in the art may use known injectable, physiologically acceptable sterile solutions. For preparing a ready-to-use solution for parenteral injection or infusion, aqueous isotonic solutions, for example, saline, phosphate buffered saline (PBS) or corresponding plasma protein solutions, are readily available. The vaccine compositions may be present as lyophylisates or dry preparations, which can be reconstituted with a known injectable solution directly before use under sterile conditions, for example, as a kit of parts. In addition, the immunogenic and vaccine compositions of the present invention can include one or more acceptable carriers (which may include, for example, solvents, dispersion media, coatings, adjuvants, stabilizing agents, diluents, preservatives, antibacterial and antifungal agents, isotonic agents, adsorption delaying agents, and the like. "Diluents" can include water, saline, PBS, dextrose, ethanol, glycerol, and the like. Isotonic agents can include sodium chloride, dextrose, mannitol, sorbitol, and lactose, among others. Stabilizers include albumin and alkali salts of ethylenediaminetetracetic acid, among others.

Any suitable route of administration may be employed for providing a subject with an effective amount/dosage of vaccine, vaccine composition, and agents according to the representative embodiments of the invention. A suitable route of administration may be determined readily by one skilled in the art of pharmacology, immunology, medicine, or the like without undue experimentation. For example, the dosage may be administered orally, intranasally (i.n.), parenterally, topically, intravenously (i.v.), intraoccularly, by injection, subcutaneously (s.q.), or the like. It is understood that injection comprises also perfusion and continuous infusion. Dosage forms may include, for example, tablets, capsules, powders, solutions, dispersions, suspensions, ointments, and aerosols.

The following examples are provided for illustration purposes only, and are in no way intended to limit the scope of the present invention.

Example 1

Susceptibility of Cotton Rats to Infection with HRV16

Rationale and Experimental Approach

Studies were designed to demonstrate that the cotton rat is a permissive host for HRV16 and, therefore, could be used as an animal model for the development of anti-rhinovirus vaccines and therapeutics for the prevention and/or alleviation of rhinovirus-associated respiratory illnesses. Initial efforts focused on the examination of HRV16 infection, replication, and pathogenesis in the cotton rats.

Materials and Methods

Virus.

HRV16 (strain 11757, ATCC cat#VR-283) was obtained from American Type Culture Collection. Virus stocks were produced in HeLa Ohio cells and titered by plaque assay under agarose overlay in monolayers of the same cell line.

Animals.

Young adult (4-8 weeks old) cotton rats (*Sigmodon hispidus*) of both genders were obtained from the inbred colony maintained at Sigmovir Bioystems, Inc (SBI). The animals were housed in large polycarbonate cages, and fed a diet of standard rodent chow and water. Cotton rats were seronegative for adventitious respiratory viruses, and other common rodent pathogens. All experiments were performed using protocols that followed federal guidelines and were approved by SBI's Institutional Animal Care and Use Committee (IACUC). Cotton rats were infected i.n. or vaccinated i.m. with HRV16 or with various vaccines under isoflurane anesthesia by application of 0.1 ml of solution per rat. Serum was obtained by retro-orbital blood collection under isoflurane anesthesia. Animals were sacrificed by carbon dioxide asphyxiation.

Virus Titration Assay.

Tissue samples (left lung lobe, entire nose, and trachea) were homogenized in 3 ml of infection medium (MEM, 2% fetal calf serum, 1.5 g/ml sodium bicarbonate, 25 mM HEPES, penicillin and streptomycin) using a glass-to-glass homogenizer (lung and trachea) or mortar and pestle (nose), centrifuged at 2,000 rpm to precipitate debris, and frozen at $-80°$ C. until titration by plaque assay. Infectious virus titers were determined by standard plaque assay in HeLa Ohio cells and expressed in plaque forming units (PFU)/g of tissue.

Antibody Assay.

Neutralizing antibody titers were determined by a plaque-reduction neutralization assay, using a 60% plaque reduction endpoint. Briefly, serial 4 fold dilutions of serum were incubated with an equal volume of virus stock containing approximately 60 PFU per 100 μl. Stock incubated with PBS was used as control. After 1 h of incubation, at 37° C., neutralization mixes were plated in 4 replicates onto wells of 24-well plates, incubated at 33° C. for 1 h and then overlayed with a 1:1 mixture of 1.4% Low Melt Agarose (Bioexpress Catalog #E-3111-125) and 2×MEM (Gibco Catalog #11935) supplemented with 1M $MgCl_2$ (Sigma Catalog #M8266), 2% Penicillin/Streptomycin (Gibco Catalog #15140), 2% L-Glutamine (Gibco Catalog #25030) and 4% Newborn Calf Serum (Gibco Catalog #26010). Plaque reduction assays were incubated at 33° C. and 5% $CO_2$ for 48 hours then fixed with 1% formaldehyde (Sigma Catalog #F-8775) in 0.15M NaCl (Sigma Catalog #S-3014). Fixed assays were stained with crystal violet (Sigma Catalog #HT901) for 1 h, rinsed and dried before reading.

RNA Isolation and RT-PCR Analysis.

Lungs were dissected for RNA isolation using RNeasy (Qiagen). BAL cells were collected with cold saline, pelleted and lysed with 0.7 ml of buffer RLT with $^2$-mercaptoethanol. RNA was isolated from BAL and from the lingular lobe (small left lobe) of the lung using RNeasy Kit (Qiagen #74106). cDNA was prepared by using QuantiTect Reverse Transcription Kit (Qiagen Catalog #205314). At the end of reaction cDNA was diluted with water to keep ratio 1 μg of initial RNA per 100 μl of final cDNA volume. Three μl of diluted cDNA per reaction was used for real-time PCR in single copies. A HRV16-specific qPCR protocol was developed using primers that target the 5' UTR of HRV-16 (GenBank ACC#L24917). In order to quantify total viral genome (positive strand), cDNA was synthesized by priming with the following primer: 5'-AAACACGGACACGGACAC-CCAAAG-3' (SEQ ID NO:1). To quantify the replication intermediate negative strand (as an indicator of active viral replication), cDNA was synthesized by priming with following primer: 5'-CCCTTTCCCAAATGTAACTTAGAAGC-3' (SEQ ID NO:2). When indicated, cDNA was also generated using oligo-dT primers. All primers were used at a concentration of 0.5 μg/ml, and 1 μl of each primer was used in a cDNA reaction of 20 μl containing 1 μg of total RNA, and SuperScript II RT (Invitrogen) and incubated for 75 minutes at 72° C. Real-time PCR quantification of both strands was performed using the following primer pair: forward primer: 5-TCAAGCACTTCTGTTTCCCCGGT-3' (SEQ ID NO:3); reverse primer: 5'-TCCCATCCCGCAATTGCTCATTAC-3' (SEQ ID NO:4), generating a fragment of 370 bp.

Statistical Analysis.

Viral titers were calculated as geometric means±standard error for all animals in a group at a given time post infection. Pulmonary scores were expressed as the arithmetic mean±standard error for all animals in a group.

Results

Figure 1B:
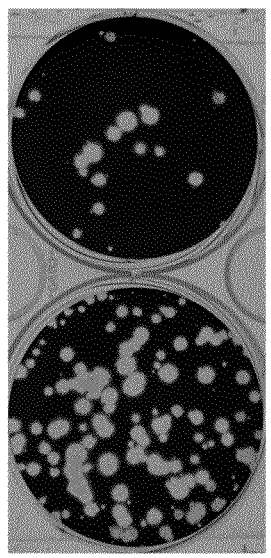
FIG. 1B depicts a representative HRV16 plaque quantification assay of lung homogenates of infected cotton rats in HeLa Ohio cells.

Cotton rats were infected i.n. with HRV16 using $10^7$ PFU/animal. Groups of animals were sacrificed at 0.5, 2, 4, 6, 8, and 10 h, and at day 1, 2, and 4 post-infection (FIG. 1A). A group of non-infected animals or animals inoculated with UV-inactivated HRV16 were used as control. At the indicated times post-infection, nose, trachea, and lung tissue were isolated for assessment of viral load by plaque assay (FIG. 1B). Infectious HRV16 was recovered from the nose and trachea until day 1 post-infection, and from the lung until day 2 post-infection. No infectious virus was detected in any of the tissues analyzed on day 4 post-infection. Virus titers were higher in the lungs ($>10^7$ PFU/gr of tissue), followed by the nose and the trachea ($\sim 10^6$ PFU/g of tissue). A brief plateau between 6-10 h post-infection and a subsequent decrease and clearance of virus were detected in the nose and trachea. Intranasal infection with HRV16 at a lower inoculum ($10^6$ PFU/animal) rendered lung viral titers of $5.9 \times 10^5 \pm 8.6 \times 10^4$ PFU/g at 8 h post-infection (n=16), with no detectable virus at 48 h post-infection (data not shown) indicated that the cotton rat is a semi-permissive model for HRV16 infection.

Figure 1C:
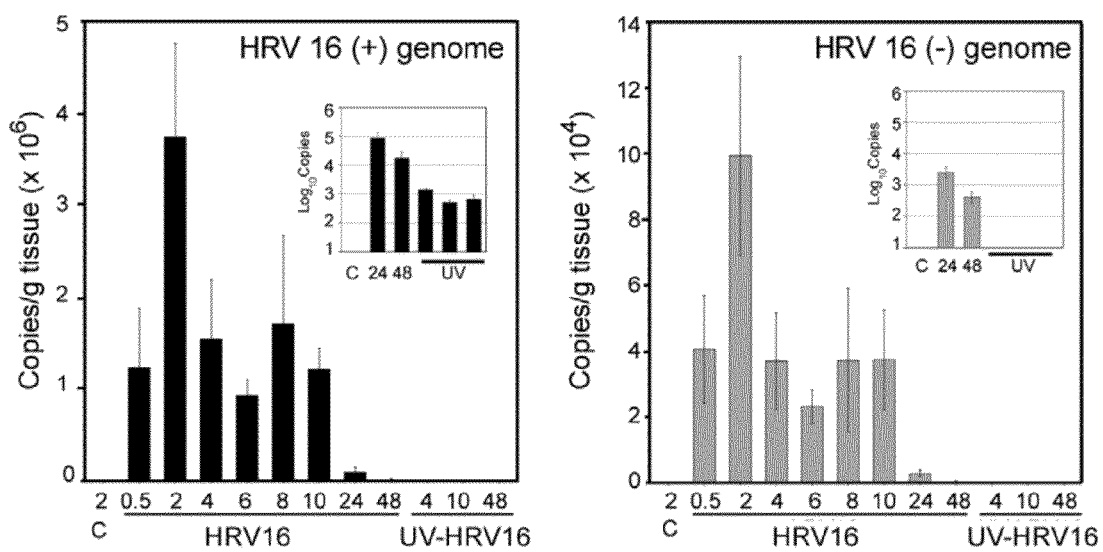
FIG. 1C shows the quantification of HRV16 positive and negative genome by reverse transcriptase-polymerase chain reaction (RT-PCR) in lung tissue at the indicated times post infection. Animals inoculated with ultraviolet light (UV)-inactivated HRV16 were used as control. Inserts are blow out of the 24 and 48 h time points from HRV16-infected and UV-HRV16 inoculated animals using logarithmic scale (n=5 per time point).

To better determine the kinetics of viral replication, we quantified the presence of positive strand viral genomic RNA and the replication intermediate negative stranded viral RNA (FIG. 1C). Both strands were detected in RNA samples obtained from lungs of infected animals until 48 h post-infection (FIG. 1C, insets). By comparing the expression of positive and negative strand genomes, the number of copies of negative genome (replication intermediates) was approximately 25-fold lower than the number of copies of positive strand detected. As expected, animals inoculated with UV-inactivated HRV16 ($10^7$ PFU) showed low but detectable amounts of positive strand genomes but undetectable negative, replication intermediate HRV-16 RNA strands.

Example 2

Histopathology and Mx Gene Expression in HRV16-Infected Cotton Rats

Rationale and Experimental Approach

Studies were designed to characterize pathological changes in cotton rats following infection with HRV16.

Materials and Methods

Virus.

HRV16 and virus stocks were obtained and produced as described above.

Animals.

Cotton rats were obtained and maintained as described above.

Analysis of Mx Gene Expression.

The assessment of cotton rat Mx-1 and Mx-2 gene expression was carried out as previously described (Pletneva et al., *J. Interferon Cytokine Res.* 26:914, 2006; Pletneva et al., *J. Gen. Virol.* 89:261, 2008).

Statistical Analysis.

Analysis was performed as described above.

Results

Figure 2A:
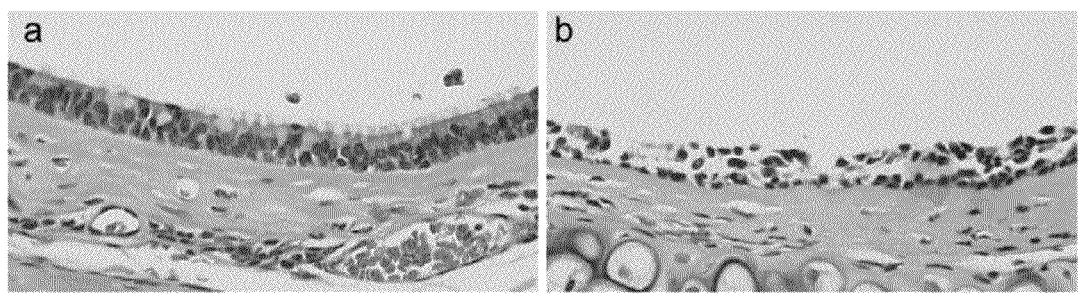
FIG. 2A depicts tracheal epithelial cell defoliation in uninfected cotton rat (panel a) and HRV16-infected cotton rat (panel b) at 100× magnification.

Analysis of the pathology associated with HRV16 infection was performed in nose, trachea, and lung using conventional H&E stain and Alcian blue-PAS staining for mucus detection. Lesions were graded on a 5-point scale (0=absent, 1=minimal, 2=mild, 3=moderate, 4=marked). No significant lesions (beyond some minimal inflammation in one specimen) were noted in the nasal sections. Epithelial degeneration was present in tracheal epithelium from HRV16-infected rats, and was extended to some of the large pulmonary airways. Infection was associated with direct and progressive damage of the ciliated columnar epithelium of the trachea peaking on day 4 post-infection and in many cases exposing the basal membrane (FIG. 2A).

Figure 2B:
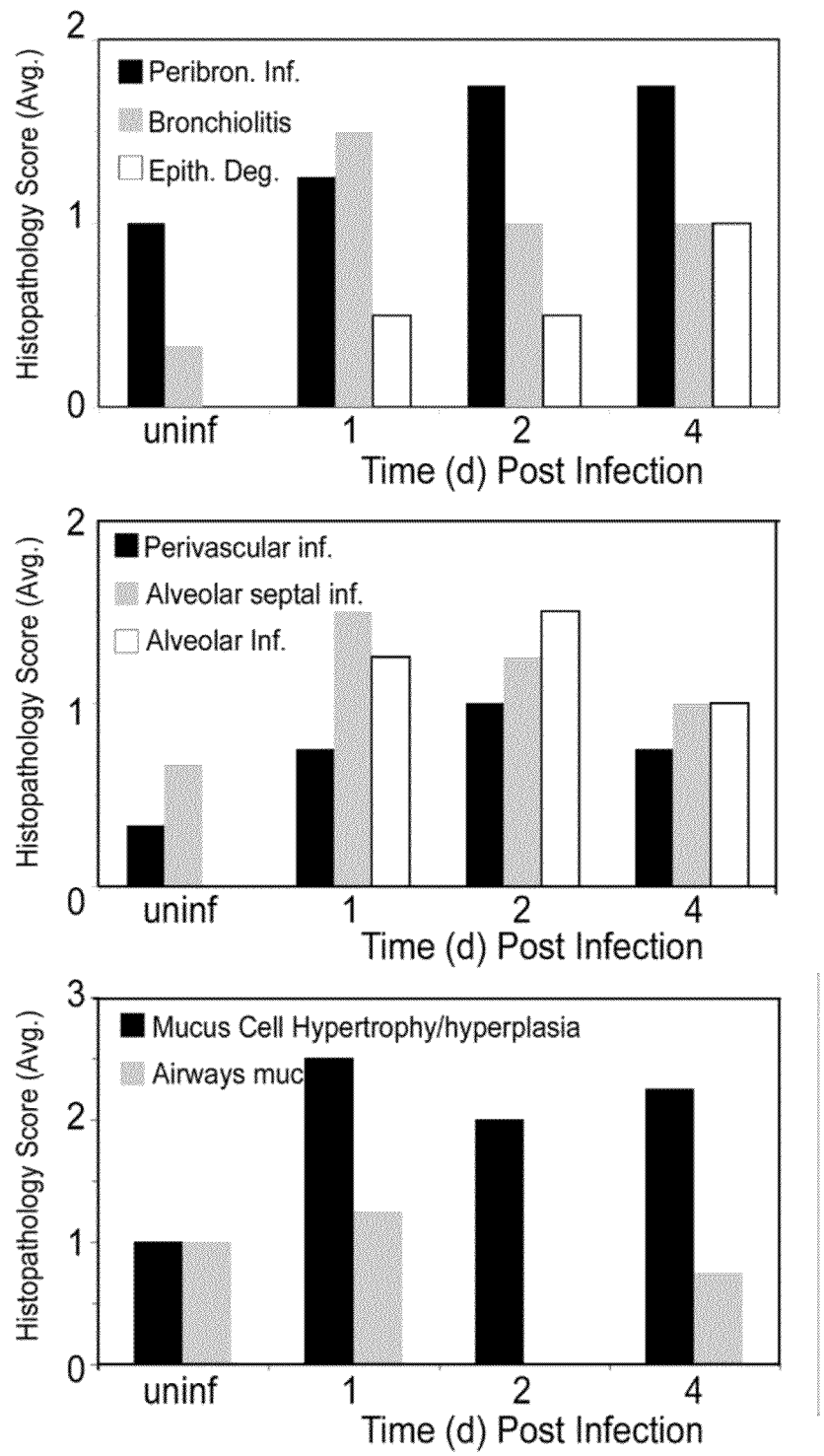
FIG. 2B shows histopathology scores obtained from lungs of uninfected animals (uninf.) and animals infected with HRV16 and sacrificed at the indicated times post-infection. Graphs represent the mean scores (n=4) of the extent of peribronchiolar infiltration, bronchiolitis, and epithelial degeneration (top panel); perivascular infiltration, alveolar septal infiltration and alveolar infiltration (middle panel); and mucus cell hypertrophy/hyperplasia.
Figure 2C:
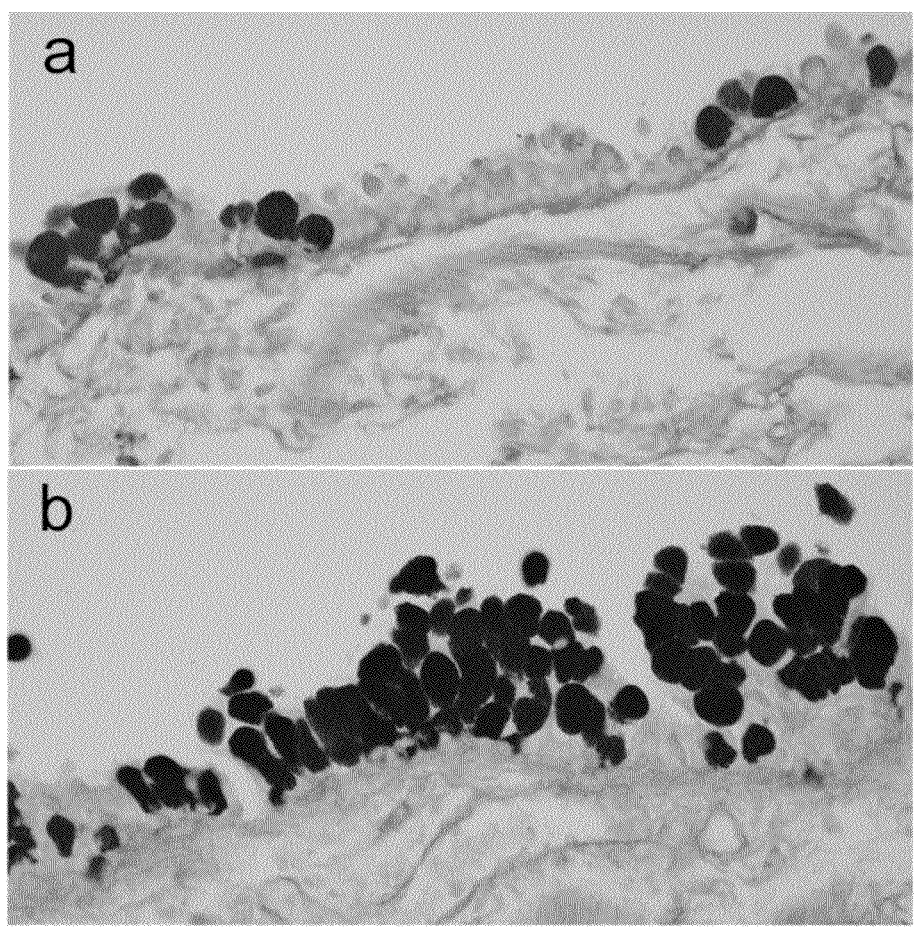
FIG. 2C shows Alcian blue-PAS staining of a bifurcation of the main axial airway of an uninfected (panel a) and an HRV16-infected cotton rat (panel b).

Analysis of lung pathology demonstrated mild alveolitis (neutrophilic and histiocytic), and mild peribronchiolar infiltrates of neutrophils, macrophages, and lymphocytes (FIG. 2B). In some cases, animals exhibited mild bronchiolitis characterized by neutrophil transmigration across the mucosal epithelium. Also, there was evidence of bronchiolar epithelial degeneration characterized by epithelial cytoplasmic vacuole formation and apical blebbing along with multifocal attenuation of the mucosal epithelium and occasional cell drop out. In some areas of alveolitis, histiocytic erythrophagocytosis was present along with scattered red blood cells (RBCs) in alveolar spaces (evidence of minimal hemorrhage). Mucous cell hypertrophy/hyperplasia was evident in H&E- and AB-PAS-stained lung sections as early as 1-day post-infection (FIG. 2C). Overall the data show that HRV16 infection in the cotton rat reproduces aspects of human disease in the upper respiratory tract (URT) and produces detectable inflammation in the lower airways and lung parenchyma.

In contrast with other respiratory viral infections, such as influenza in the cotton rat (Ottolini et al., *J. Gen. Virol.* 86:2823, 2005; Blanco et al., *J. Virol.* 87:2036, 2013), HRV infection result only in mild epithelial damage (vacuolar degeneration, apical blebbing in the bronchioles, sloughing in the trachea), correlating with previous observations in humans (Winther et al., *Acta Otolaryngol.* 97:309, 1984; Winther et al, *Am. Rev. Respir. Dis.* 141:839, 1990). The time required for a complete replication cycle of human rhinovirus to occur is 5 to 10 h (Racaniello. Picornaviridae, *Virology*, Vol. 1, Lippincott-Williams & Wilkins, Philadelphia, Pa., 2007). The course of infection appears to be similar in the cotton rat where we detected a pause in the production of negative strands at ~6 h post-infection and later, a second wave of replication occurring ~ at 8-10 h.

Figure 2D:
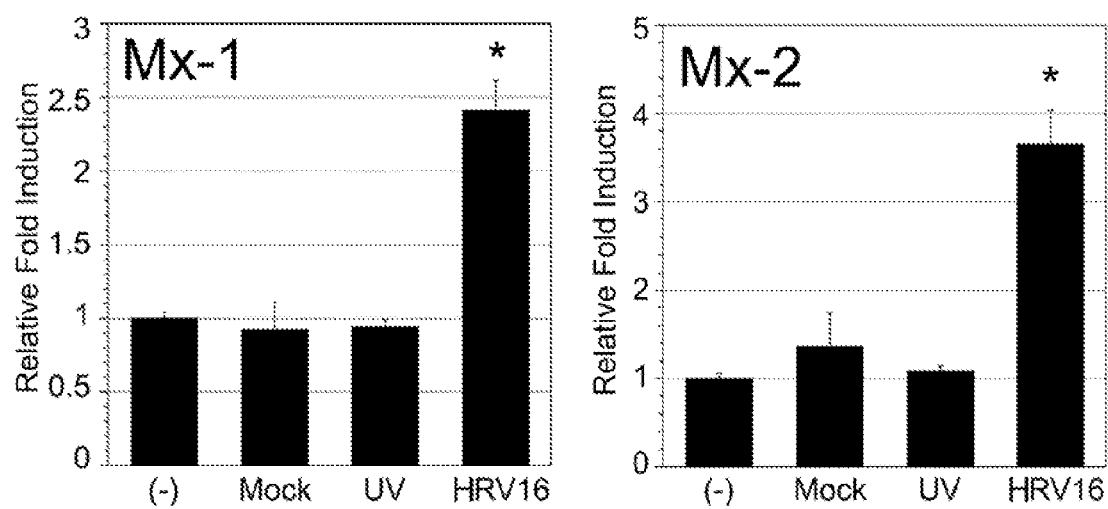
FIG. 2D shows quantitative polymerase chain reaction (qPCR) quantification of the expression of cotton rat Mx-1 and Mx-2 in bronchioalveolar lavage (BAL) cells from cotton rats that were uninfected, mock-inoculated, inoculated with UV-inactivated HRV16, and inoculated with live HRV16 (n=8 per group; *represents p<0.005 in Student t-test analysis between HRV16 infected group and each of the control groups).

We measured the expression of cotton rat Mx1 gene (the homologue of human MxA) and cotton rat Mx-2 (Pletneva et al., *J. Interferon Cytokine Res.* 26:914, 2006; Pletneva et al., *J. Gen. Virol.* 89:261, 2008) in response to HRV16 infection in the lung of cotton rats. In vivo, the expression of Mx1 is an indicator of presence of type I interferons and its induction has been studied during HRV infection in humans (Proud et al., *Am. J. Respir. Crit. Care Med.* 178:962, 2008; Makela et al., *Eur. J. Clin. Microbiol. Infect. Dis.* 18:665, 1999) and human bronchial epithelial cells (Gielen, et al., *Eur. Respir. J.* 36:646, 2010). HRV16 activated the expression of Mx-1 and Mx-2 in BAL cells of cotton rats at 6 h post-infection (FIG. 2D). The increase in the expression was not detected in lung samples, suggesting that cells intimately associated with the airways, rather than with the lung parenchyma, were most likely to induce Mx expression upon infection. This result strikingly parallels the detection of the expression of Mx1 (MxA) and Mx2 genes in nasal epithelial scrapings obtained 8 h after experimental HRV16 infection in humans (Proud et al., *Am. J. Respir. Crit. Care Med.* 178:962, 2008). Analysis of subsequent time points (12 and 24 h) did not show any significant change in the expression when compared to controls, mock inoculated animals or animals inoculated with UV-inactivated HRV16 indicating that the induction of interferon was transient.

Although the biological bases for the cotton rat's distinct susceptibility to human viral infections are not fully understood, cotton rats are New World rodents of the Cricetidae family, in contrast to the laboratory mouse (Mus species) and rat (*Rattus* species), which are Old World rodents of the Muridae family. Importantly, unlike the laboratory mouse, which either lacks or has defective Mx genes, the cotton rat has a set of fully functional Mx genes. Mx proteins are GTPases with antiviral activity against a wide range of RNA viruses (Haller et al., *Rev. Sci. Tech.* 17:220, 1998), including influenza (Haller et al., *J. Exp. Med.* 149:601, 1979; Haller and Kochs. Traffic 3:710, 2002). In vivo, Mx gene expression is tightly regulated by the presence of type I interferons (IFNs). In cotton rats, the expression of Mx genes responds to infection with influenza and RSV as it has been described for the human Mx counterparts (Pletneva et al., *J. Interferon Cytokine Res.* 26:914, 2006; Pletneva et al., *J. Gen. Virol.* 89:261, 2008), and the anti-influenza activity of human MxA was confirmed for the cotton rat Mx1 protein (Stertz et al., *J. Interferon Cytokine Res.* 27:847, 2007).

Example 3

HRV16 Immunity in Cotton Rats

Rationale and Experimental Approach

Studies were designed to examine the ability to vaccinate cotton rats against HRV16 infection.

Materials and Methods

Virus.

HRV1B (ATCC cat#VR-1645) and HRV16 (strain 11757, ATCC cat#VR-283) were obtained from ATCC. Virus stocks were produced in HeLa Ohio cells and titered by plaque assay under agarose overlay in monolayers of the same cell line.

Animals.

Cotton rats were obtained and maintained as described above.

Antibody Assay.

Neutralizing antibody titers were determined by a plaque-reduction neutralization assay as described above.

Statistical Analysis.

Analysis was performed as described above.

Results

Figure 3A:
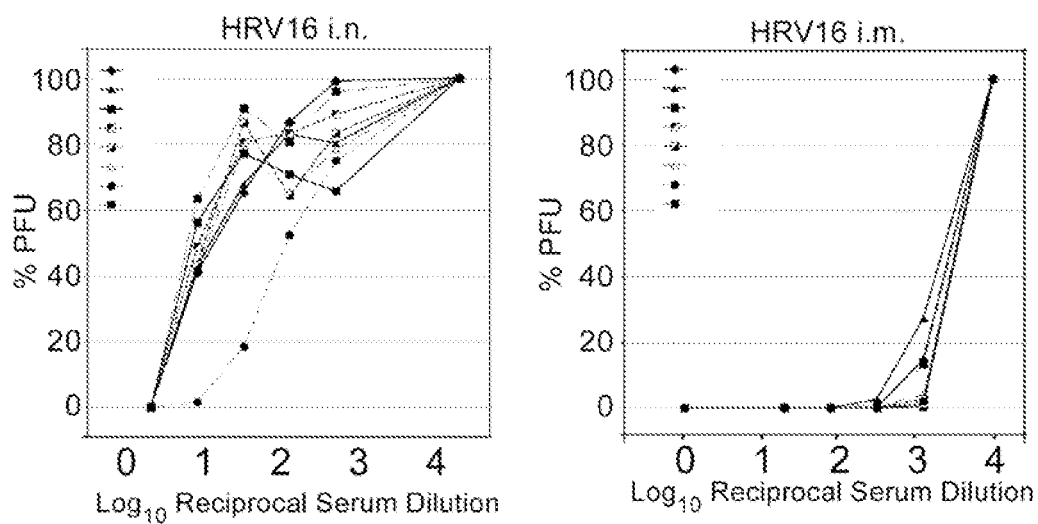
FIG. 3A shows HRV16 neutralizing activity in serum from animals infected intranasally twice with HRV16 (left panel) or in serum of animals vaccinated and boosted intramuscularly with the same live virus (right panel). Each curve represents a serum neutralization profile of a single animal.
Figure 3B:
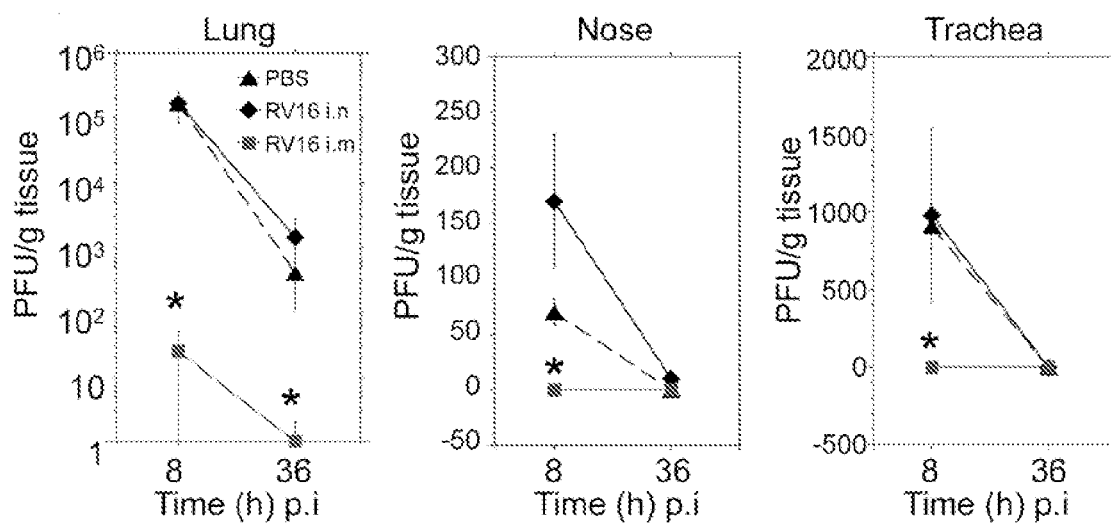
FIG. 3B shows viral titers of the lung, nose, and trachea of animals challenged with HRV16 twenty one days after treatment with PBS i.m., infection with HRV16 i.n., or vaccination with HRV16 i.m. n=5 per group and per time-point.
Figure 3C:
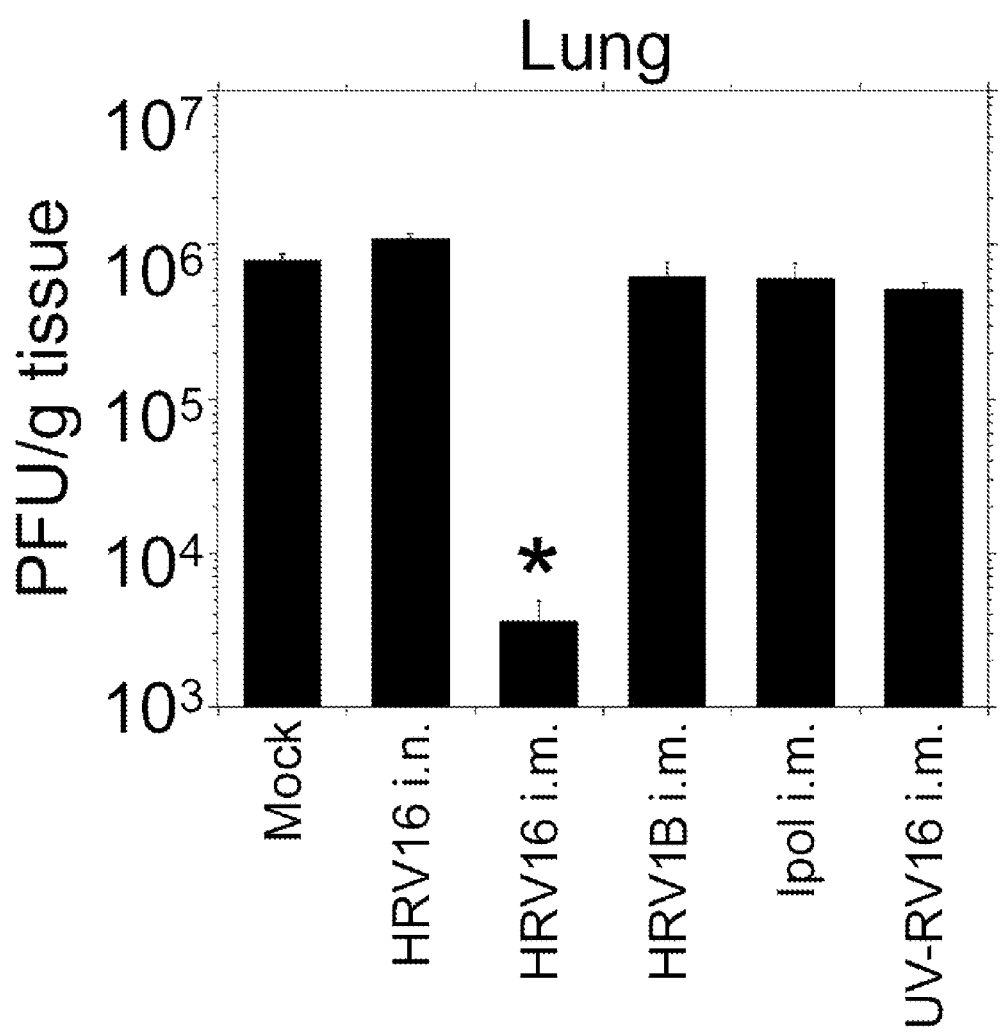
FIG. 3C shows lung viral titers from animals challenged with HRV16 after vaccination with different vaccine preparations.

Intramuscular (i.m.) vaccination with live HRV16 at a dose of $10^7$ PFU in a priming (day 0) and boosting (day 21) schedule induced the development of high levels of serum neutralizing antibody in cotton rats when measured on day 42 post-priming (FIG. 3A, right panel). Surprisingly, that was not the case when the same amount of virus was instilled i.n. following an identical schedule (FIG. 3A, left panel). All animals vaccinated i.m. showed reciprocal of neutralizing antibody titers >1,280 in the 60% plaque reduction assay, whereas animals that underwent infection or re-infections with HRV16 showed low neutralizing antibody titers that were in the range of 4-16. Furthermore, when animals immunized with a single i.m. inoculation of HRV16 were challenged 21 days later i.n. with $10^7$ PFU of HRV16, infectious virus was not detected in the nasal turbinates or in the trachea, and >3 $\log_{10}$ reduction of infectious virus titers was detected in the lung (FIG. 3B). Intramuscular vaccination was only effective when live HRV16 was used for inoculation. Vaccination with live HRV1B, or UV-inactivated HRV16 in the same amount, or with a current polio vaccine (Ipol), did not confer any measurable protection against HRV16 challenge (FIG. 3C).

Figure 3D:
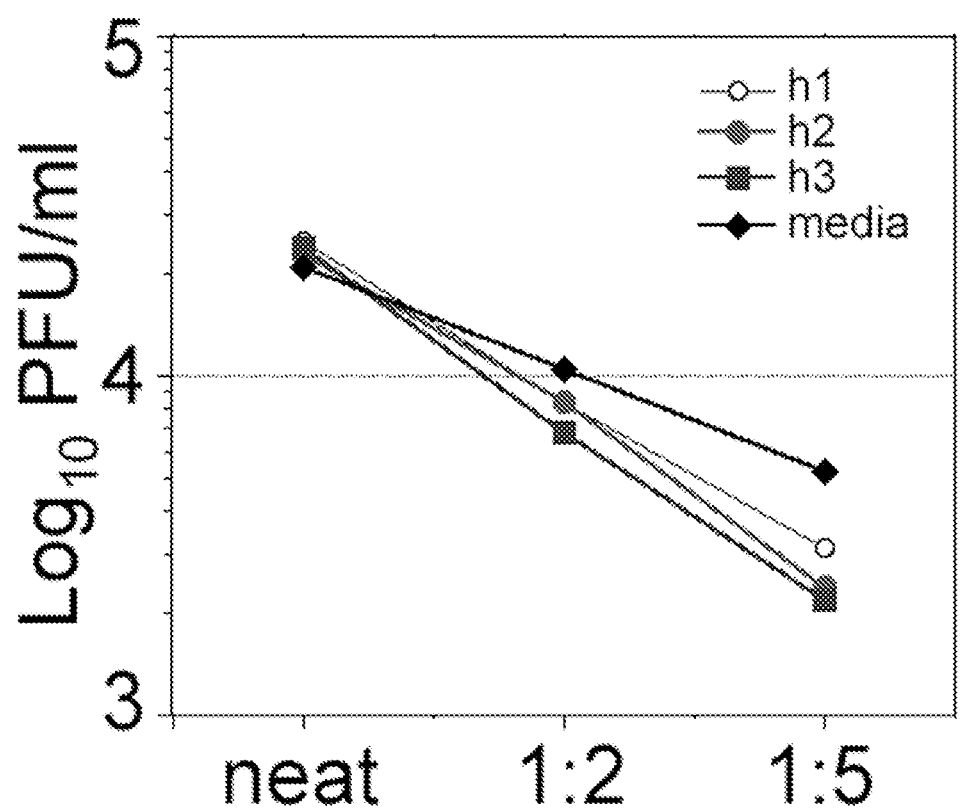
FIG. 3D shows that neutralization of viral replication occurs in vivo. Lung homogenates from animals vaccinated with PBS (positive control agent) and animals vaccinated i.m. with HRV16 (neutralization titers >1,280) were admixed and used to determine whether neutralization of HRV16 was the product of ex vivo neutralization. Plaque reduction of all mixes followed the dilution curve and was not consistent with neutralization occurring ex vivo.

Conceivably, reduction of the viral titers in tissues of animals vaccinated i.m. could result from in vitro neutralization that occurs during homogenization of the tissue. This possibility was investigated by mixing lung homogenates obtained from rats immunized with HRV16 i.m. with similar homogenates obtained from naïve rats, all challenged with HRV16 and sacrificed at 8 h post-challenged. Titration of these mixed homogenates in different proportions showed that viral loads were compatible with those predicted by the corresponding dilution of the virus (1:2 and 1:5 respectively) and not attributable to the presence of in vitro neutralization (FIG. 3D). This result indicates that i.m vaccination with life virus induces bona fide in vivo viral neutralization of HRV16.

Example 4

Passive Transfer of Anti-HRV16 Immune Serum Protects Against HRV16 Challenge

Rationale and Experimental Approach

It was previously demonstrated that parenteral administration to cotton rats of convalescent antisera with high neutralizing antibodies titers against Respiratory Syncytial Virus (RSV) prior to challenge provided near-complete protection from pulmonary infection (Prince et al., J. Virol. 55:517, 1985). Currently, prophylactic therapy with hyper-immune anti-RSV monoclonal antibodies is the only efficacious treatment against RSV disease in high-risk infants. Following a similar rationale, experiments were designed to test the efficacy of immune (neutralizing antibody titer of 1:1,280 against HRV16) or normal cotton rat serum given prophylactically in different concentrations to protect against HRV16 challenge in cotton rats.

Materials and Methods

All materials and methods were as described above.

Results

Figure 4:
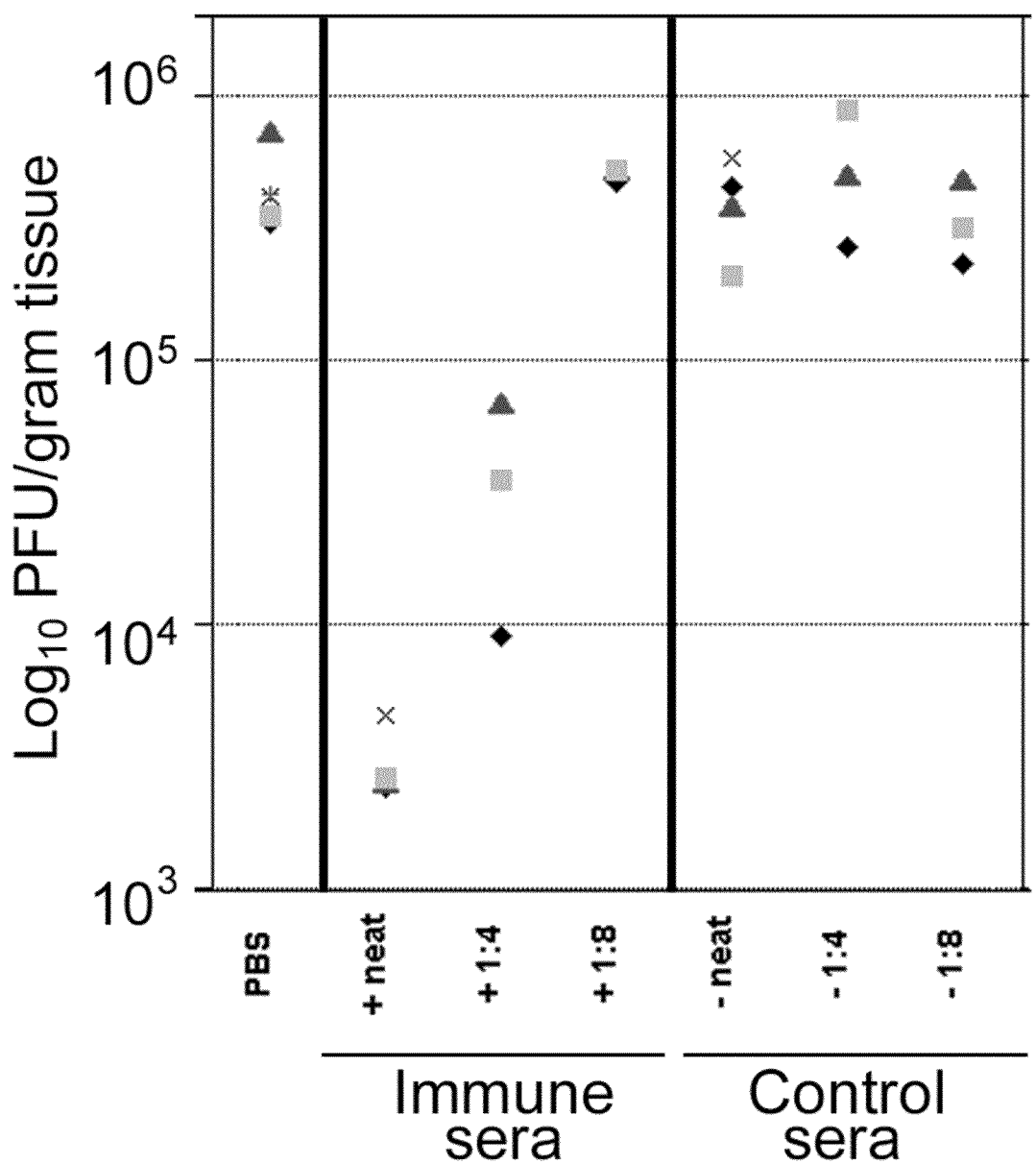
FIG. 4 shows that passive transfer of antibodies against HRV16 protects animals from HRV16 challenge. Animals were treated intraperitoneally (i.p.) with 500 µl of a control cotton rat serum (HRV16 neutralization titers <1:20) or with different dilutions of HRV16 immune serum that was obtained from animals vaccinated i.m. with HRV16 ($10^7$ PFU). One day post-treatment, animals were challenged with HRV16 i.n., and sacrificed at 8 h later to determine lung viral titers.

Neutralizing antibody titers detected in animals prior to challenge are shown in Table 1. All animals that received undiluted sera (neat) or serum diluted 1:4 showed a reduction of lung viral titers of 2 and 1 $\log_{10}$, respectively, whereas animals that received more diluted immune serum (1:8), normal cotton rat serum, or PBS, remained unprotected (FIG. 4). These data indicate that passive transfer of antibodies can be a potential therapy against HRV infections.

TABLE 1

Prophylactic effect of anti-HRV16 serum on HRV16 infection in cotton rats.

| Serum Inoculated i.p | No. of rats | Serum neutralizing antibodies at the time of challenge (geometric mean, reciprocal ± S.E.)[a] | Lung titer of virus 12 h after challenge with $10^7$ pfu of HRV16 (geometric mean $\log_{10}$ pfu/g ± S.E.)[b] |
|---|---|---|---|
| Control serum (neutralizing antibody titer <1:20) | 10 | <1:20 | -6.1 ± 0.12 [c] |
| Immune serum (neutralizing antibody titer 1:1280) | 4 | 340 ± 96 | -3.9 ± 0.12 [d] |
| (neutralizing antibody titer 1:320) | 3 | 104 ± 52 | 4.9 ± 0.22 |
| (neutralizing antibody titer 1:160) | 3 | 55 ± 32 | 6.1 ± 0.23 |

[a]Measured by plaque assay reduction against HRV16 and expressed as reciprocal of the geometric mean. Serum was collected one day post-treatment.
[b]Measured by plaque assay.
[c]p <0.005
[d]p <0.01

Example 5

Maternal Vaccination Against HRV Protects Offspring Against Infection with HRV

Rationale and Experimental Approach

Experiments were designed to determine if serum antibodies passed from immunized mothers to offspring can protect offspring against human rhinovirus infection or rhinovirus-associated illness.

Materials and Methods

All materials and methods were as described above.

Results

Figure 5A:
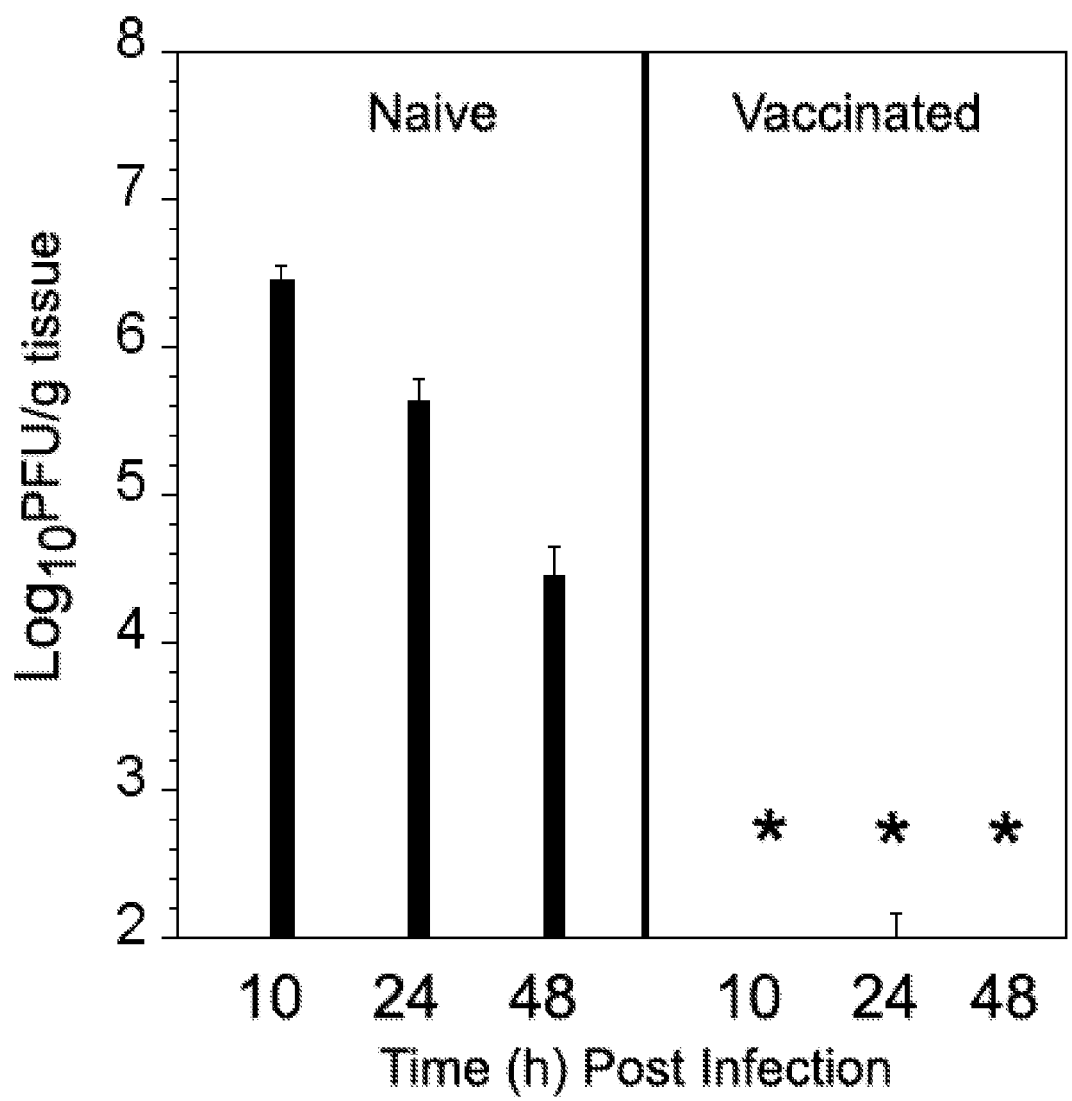
FIG. 5A shows viral titers in three- to five-day old newborns that were challenged i.n. with HRV16 and were offspring of naïve females (left panel) or females vaccinated i.m. with HRV16 (right panel). Titers were measured at the indicated time post-infection.
Figure 5B:
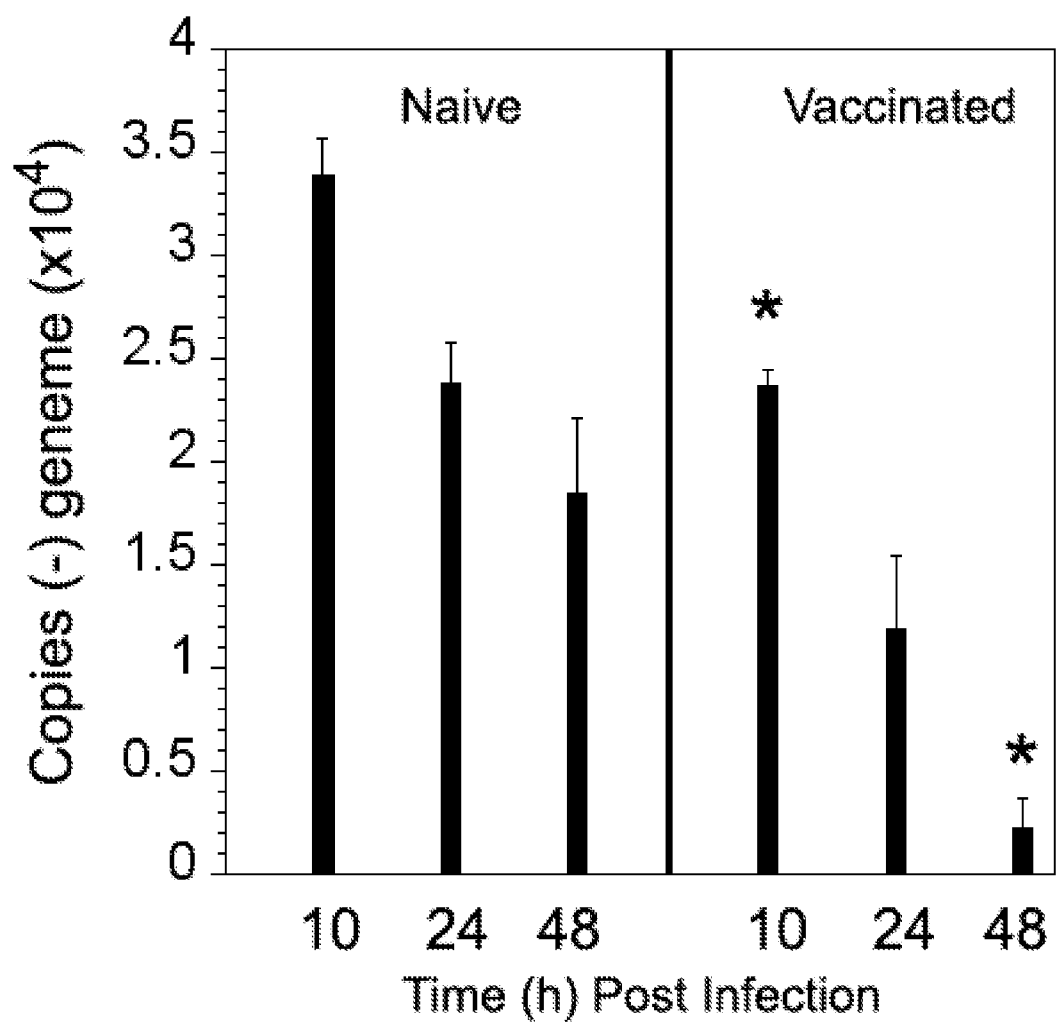
FIG. 5B shows HRV16 (−) genome detection in lung tissue from newborn cotton rats that were challenged i.n. with HRV16 and were offspring of naïve females (left panel) or females vaccinated i.m. with HRV16 (right panel). n=6-8 animals/group where each group consisted of pups from 2 different mothers. * $p<0.05$ in Student t-test comparison between group of pups whose mothers were vaccinated versus groups of pups of the same age from unvaccinated, naïve mothers.

Young female cotton rats were vaccinated twice i.m. with HRV16 and on day 42, they were set in mating pairs. Newborns delivered from vaccinated or unvaccinated females were challenged between the ages of 3 to 5 days with HRV16 i.n. and sacrificed at 10, 24, and 48 h post-infection. Pups from unvaccinated mothers showed lung HRV16 titers that were similar to those of adult cotton rats (FIG. 5A). Pups from vaccinated mothers showed >3 $\log_{10}$ reduction in the viral titers measured in the lungs (FIG. 5A). Results were paralleled by determination inhibition of viral replication in the lung by repression of production of negative HRV16 genome (FIG. 5B). Overall the data indicate that there is an efficient maternal transfer of immunity against HRV16 to newborns, and that immunity against HRV in mothers is conferred by vaccination.

CONCLUSIONS DERIVED FROM EXAMPLES

The Examples disclosed herein demonstrate (1) consistent and reproducible detection and quantification of HRV16 infectious loads in the upper (U) and lower (L) respiratory tract (RT) of cotton rats infected i.n. with HRV16, (2) detection of steady-state levels of HRV16 genomic RNA in lungs of infected animals, (3) pathology associated with HRV16 in the URT and LRT of cotton rats, (4) activation of the expression of interferon-activated genes (Mx-1 and Mx-2) in the BAL cells from lungs of cotton rats upon HRV16 infection, (5) identification of a vaccination route for protection of cotton rats against HRV16 challenge, and (6) determination of the protective effect of passive transfer of antibodies against HRV16 against challenge. Therefore, the Examples establish that the cotton rat is a permissive host for HRV16. HRV16 infection in the cotton rat reproduces aspects of human disease in the URT, causes detectable inflammation in the lower airways and lung parenchyma, and induces expression of interferon-stimulated genes. Accordingly, and as set forth in the various representative embodiments of the invention, cotton rats can be a valuable model for the study of infection, pathogenesis, and immunity of HRV, and cotton rats can be used in challenge studies to explore, identify, and develop anti-rhinovirus vaccines and therapies.

Each reference referred to within this disclosure is hereby incorporated in its respective entirety.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, because numerous modifications will readily occur to those skilled in the art, it is not desired to limit the invention to the exact construction and operation illustrated and described, and accordingly, all suitable modifications and equivalents may be resorted to, falling within the scope of the invention.

We claim:

1. A method of identifying or testing a vaccine or therapeutic agent that reduces rhinovirus A (HRV-A) infection and/or reduces rhinovirus B (HRV-B) infection, comprising:
   measuring the titer of HRV-A and/or HRV-B in lung derived from cotton rats challenged with HRV-A and/or HRV-B intranasally after administration of a potential HRV-A and/or HRV-B vaccine or therapeutic agent as a first test sample;
   measuring the titer of HRV-A and/or HRV-B in lung derived from cotton rats challenged with HRV-A and/or HRV-B intranasally after administration of a control agent as a second test sample; and
   determining whether there is a decrease in the titer of HRV-A and/or HRV-B in said first test sample as compared to said second test sample,
   wherein a decrease in the titer of HRV-A and/or HRV-B in said first test sample is indicative of the identification of a vaccine or therapeutic agent that reduces HRV-A infection and/or reduces HRV-B infection.

2. The method of claim 1, wherein said potential HRV-A and/or HRV-B vaccine or therapeutic agent is a native protein or a fragment thereof.

3. The method of claim 1, wherein said potential HRV-A and/or HRV-B vaccine or therapeutic agent is a recombinant protein or a fragment thereof.

4. The method of claim 1, wherein said potential HRV-A and/or HRV-B vaccine or therapeutic agent is a nucleic acid.

5. The method of claim 1, wherein said potential HRV-A and/or HRV-B vaccine or therapeutic agent is a receptor.

6. The method of claim 1, wherein said potential HRV-A and/or HRV-B vaccine or therapeutic agent is a small molecule.

7. The method of claim 1, wherein said administration of a potential HRV-A and/or HRV-B vaccine or therapeutic agent is selected from the group consisting of intramuscular, intradermal, intravenous, subcutaneous, and oral.

8. The method of claim 1, wherein said administration of a potential HRV-A and/or HRV-B vaccine or therapeutic agent is achieved intramuscularly.

9. The method of claim 1, wherein said control agent is selected from the group consisting of saline, phosphate buffered saline (PBS), inert aqueous isotonic solutions, and ultraviolet light (UV)-inactivated HRV-A, and UV-inactivated HRV-B.

10. The method of claim 1, wherein said control agent is phosphate buffered saline (PBS).

* * * * *

```
SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Synthetic construct; primer

<400> SEQUENCE: 1
aaacacggac acggacaccc aaag                                              24

<210> SEQ ID NO 2
<211> LENGTH: 26
<212> TYPE: DNA
<213> ORGANISM: Artificial Sequence
<220> FEATURE:
<223> OTHER INFORMATION: Synthetic construct; primer

<400> SEQUENCE: 2
ccctttccca aatgtaactt agaagc                                            26

<210> SEQ ID NO 3
<211> LENGTH: 23
<212> TYPE: DNA
<213> ORGANISM: Artificial Sequence
<220> FEATURE:
<223> OTHER INFORMATION: Synthetic construct; primer

<400> SEQUENCE: 3
tcaagcactt ctgtttcccc ggt                                               23

<210> SEQ ID NO 4
<211> LENGTH: 24
<212> TYPE: DNA
<213> ORGANISM: Artificial Sequence
<220> FEATURE:
<223> OTHER INFORMATION: Synthetic construct; primer

<400> SEQUENCE: 4
tcccatcccg caattgctca ttac                                              24
```